US010525291B2

(12) United States Patent
Hopermann et al.

(10) Patent No.: US 10,525,291 B2
(45) Date of Patent: Jan. 7, 2020

(54) CONNECTION MODULE, MAINTENANCE DEVICE AND METHOD FOR MAINTAINING A CLOSED-CIRCUIT BREATHING APPARATUS

(71) Applicant: Dräger Safety AG & Co. KGaA, Lübeck (DE)

(72) Inventors: Hermann Hopermann, Kastorf (DE); Jürgen Unger, Ahrensfelde (DE); Marcus Romba, Ratzeburg (DE); Mohamed Houssem Harbi, Stockelsdorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1066 days.

(21) Appl. No.: 14/925,189

(22) Filed: Oct. 28, 2015

(65) Prior Publication Data

US 2016/0121145 A1 May 5, 2016

(30) Foreign Application Priority Data

Oct. 29, 2014 (DE) .......................... 10 2014 015909

(51) Int. Cl.
*A61L 2/00* (2006.01)
*B01D 47/08* (2006.01)
(Continued)

(52) U.S. Cl.
CPC ...................................... *A62B 9/04* (2013.01)

(58) Field of Classification Search
CPC ........ A61L 2/00; A61L 2/0088; A61L 2/0094; A61L 2/022; A61L 2/16; A61L 2/20; B05C 1/00; B08B 3/04
(Continued)

(56) References Cited

U.S. PATENT DOCUMENTS

2002/0092545 A1 7/2002 Mooney
2013/0074882 A1 * 3/2013 Ackermann ........... A62B 25/00 134/36

FOREIGN PATENT DOCUMENTS

CN 1112446 A 11/1995
CN 2323798 Y 6/1999
(Continued)

*Primary Examiner* — Monzer R Chorbaji
(74) *Attorney, Agent, or Firm* — McGlew and Tuttle, P.C.

(57) ABSTRACT

A connection module (10) for installation in a closed breathing circuit of a closed-circuit breathing apparatus (1000), includes an inlet port (12), for connection to a first closed circuit element, an outlet port (14), for connection to a second closed circuit element, a maintenance fluid inlet (16), and a maintenance fluid outlet (18). A maintenance device may be provided with the connection module and a controller (30) and control module regulated valves (40). Maintenance fluid is circulated through the closed breathing circuit by the controller and valves in a state in which the connection module (10) is installed in the closed-circuit breathing apparatus. A method for maintaining a closed-circuit breathing apparatus includes opening the closed-circuit breathing apparatus at a point, installing the connection module or the maintenance device, and introducing maintenance fluid into the closed breathing circuit of the closed-circuit breathing apparatus through the connection module or the maintenance device.

16 Claims, 4 Drawing Sheets

(51) Int. Cl.
*B08B 3/00* (2006.01)
*F26B 19/00* (2006.01)
*A62B 9/04* (2006.01)

(58) Field of Classification Search
USPC ...... 422/1, 292, 300; 134/44, 56 R, 84, 105, 134/166 R, 172; 34/549; 261/38, 115
See application file for complete search history.

(56) References Cited

FOREIGN PATENT DOCUMENTS

| | | | |
|---|---|---|---|
| CN | 1586628 | A | 3/2005 |
| DE | 10 05 378 | B | 3/1957 |
| DE | 197 09 700 | A1 | 9/1998 |
| DE | 10 2010 029 221 | A1 | 11/2011 |
| DE | 10 2011 117 060 | A1 | 5/2013 |
| EP | 0 559 268 | A1 | 9/1993 |
| FR | 2 108 845 | A1 | 5/1972 |
| WO | 2012/073024 | A2 | 6/2012 |
| WO | 2013/144813 | A1 | 10/2013 |

* cited by examiner

CONNECTION MODULE, MAINTENANCE DEVICE AND METHOD FOR MAINTAINING A CLOSED-CIRCUIT BREATHING APPARATUS

CROSS REFERENCE TO RELATED APPLICATIONS

This application claims the benefit of priority under 35 U.S.C. § 119 of German Patent Application 10 2014 015909.4 filed Oct. 29, 2014, the entire contents of which are incorporated herein by reference.

FIELD OF THE INVENTION

The present invention pertains to a connection module for installation in a breathing circuit of a closed-circuit breathing apparatus, to a maintenance device for closed-circuit breathing apparatuses as well as to a maintenance system with a plurality of connection modules or maintenance systems. The present invention pertains, furthermore, to a closed-circuit breathing apparatus as well as to a method for maintaining a closed-circuit breathing apparatus.

BACKGROUND OF THE INVENTION

Closed-circuit breathing apparatuses, such as closed-circuit respirators or closed-circuit diving apparatuses, are known in the state of the art. Such closed-circuit breathing apparatuses are closed-circuit breathing apparatuses operating independently from the ambient atmosphere. They are used routinely where hazards due to toxic contaminants present in the breathing air or oxygen deficiency are to be expected. The closed-circuit breathing apparatuses, which are mostly freely portable devices, supply the user of the device with breathing gas, which is carried out, generated and purified in the closed-circuit breathing apparatus. The maximum service lives of the closed-circuit breathing apparatuses vary and depend on the quantity of breathing gas that is carried along or generated in the closed-circuit breathing apparatus as well as on the consumption of air by the user of the device.

The oxygen reserve is carried along in the closed-circuit breathing apparatus either as pressurized oxygen or as oxygen to be released from chemicals. The breathing gas exhaled by the user of the device during the operation usually flows in closed-circuit breathing apparatuses into a regenerating cartridge, in which the carbon dioxide contained in the breathing gas is chemically bound. Among other things, water and heat are generated. Closed-circuit breathing apparatuses must be intensively cleaned, disinfected and dried for hygienic reasons after each use.

For example, a cleaning device for closed-circuit breathing apparatuses, especially for demand oxygen systems and/or breathing masks, is known from DE 10 2010 029 221 A.

The maintenance of the closed-circuit breathing apparatuses requires nowadays a complicated disassembly of the closed-circuit breathing apparatuses to the smallest individual component. The components removed are then rinsed manually with tap water and subsequently cleaned and disinfected chemically. An optional drying is carried out in drying cabinets, by means of special drying nozzles for breathing tubes and/or breathing bags, or simply at ambient temperature over several days. For example, drying devices with a drying blower, which is capable of drying a plurality of closed-circuit breathing apparatuses simultaneously, are known for this purpose. The closed-circuit breathing apparatuses are partially assembled in this case completely. Nevertheless, the closed-circuit breathing apparatuses must be completely disassembled before for the cleaning and disinfection. The disassembled closed-circuit breathing apparatuses must be reassembled after drying.

Chemical or physical methods may be used to disinfect closed-circuit breathing apparatuses or breathing apparatuses. Various tested disinfectants containing different active ingredients are commercially available for the chemical methods. The physical methods include, among other things, thermal disinfection, disinfection by means of UV and UV-C radiation and plasma disinfection. Chemical or thermochemical methods are usually used in case of respirators. Thermochemical methods are employed at defined, limited temperatures with the addition of a suitable disinfectant at a corresponding concentration and with a corresponding exposure time.

The methods known in the state of the art are very time-consuming and are therefore expensive. The complete maintenance of a closed-circuit breathing apparatus including disassembly, cleaning, disinfection, drying and assembly may take several hours. Furthermore, a very large amount of water is used for the cleaning.

The disinfection is usually carried out with corrosive chemicals, which may irritate the skin of the person performing the maintenance of the device unless gloves are used. The concentrations of the cleaning agents and disinfectants as well as exposure time are strictly specified and are to be complied with. A device maintenance worker is responsible for this. Due to the manual maintenance process, the cleaning and/or disinfection parameters are often disregarded, as a result of which the components of the closed-circuit breathing apparatus may be damaged. Very small components, such as directional valves or springs, may be damaged or lost during maintenance Very small components, in particular, may be forgotten during the assembly of the closed-circuit breathing apparatus, as a result of which the ability of the closed-circuit breathing apparatus to function may be compromised.

SUMMARY OF THE INVENTION

An object of the present invention is therefore to at least partially avoid the above-described drawbacks in a maintenance device for a closed-circuit breathing apparatus as well as in a method for maintaining a closed-circuit breathing apparatus. The object of the present invention is, in particular, to provide a device as well as a method for maintaining a closed-circuit breathing apparatus, which make possible the rapid and reliable cleaning, disinfection and drying of closed-circuit breathing apparatuses.

The above object is accomplished by a connection module, a maintenance device, a closed-circuit breathing apparatus, a method for maintaining a closed-circuit breathing apparatus as well as a maintenance system according to the present invention.

According to a first aspect of the present invention, a connection module to be installed in a breathing circuit of a closed-circuit breathing apparatus is provided. The connection module has an inlet port, at which a first closed-circuit element of the closed-circuit breathing apparatus can be connected, an outlet port, at which a second closed-circuit element of the closed-circuit breathing apparatus can be connected, at least one fluid inlet, through which maintenance fluid can be introduced into the breathing circuit of the closed-circuit breathing apparatus, and at least one fluid outlet, through which the maintenance fluid can be removed from the breathing circuit of the closed-circuit breathing apparatus.

It is possible, for the first time ever, due to the connection module according to the present invention to eliminate the need for a complete disassembly of the closed-circuit breathing apparatus during maintenance, as a result of which the duration and the cost of maintenance can be considerably reduced. The connection module can be installed in the breathing circuit of the closed-circuit breathing apparatus for introducing the maintenance fluid such that it forms a closed circuit. The connection module may be plugged, screwed, brought into contact and/or mounted in a positive-locking manner by an additional fastening means for this purpose between two closed-circuit elements (e.g., between breathing passages and related components) of the closed-circuit breathing apparatus. For example, the connection module may be preferably installed between one end of an exhalation tube and a breathing bag, which are two closed-circuit elements of the closed-circuit breathing apparatus. A regenerating cartridge (CO2 absorber) may optionally be removed before in certain closed-circuit breathing apparatuses. However, it is also possible to install the connection module between one end of the exhalation tube and an inlet port of the regenerating cartridge in certain closed-circuit breathing apparatuses. However, the connection module is not limited to this and may also be installed at any other desired location between two closed-circuit elements of the closed-circuit breathing apparatus.

The connection module according to the present invention is preferably provided in this case as an essentially rigid or rigid component, which preferably consists of plastic, for example, Duroplast, and/or metal. The inlet port and the fluid inlet preferably form two separate fluid inlets with respect to the connection module. The outlet port and the fluid outlet preferably form two separate fluid outlets with respect to the connection module. In particular, the connection module has a fixed housing with defined fluid inlets and fluid outlets.

Furthermore, it is no longer possible to disregard and not to comply with the specified cleaning and disinfection times with the connection module according to the present invention. The cleaning and/or disinfection times are preset as fixed values by the duration of a flow of the maintenance fluid through the closed breathing circuit. The maintenance fluid may be, for example, a disinfecting fluid or a cleaning fluid.

A further advantage of the connection module according to the present invention is that due to the components of the closed-circuit breathing apparatus not having to be taken apart and treated separately any longer, individual components cannot be lost any more. In addition, the water consumption for cleaning the closed-circuit breathing apparatus can be reduced hereby.

Due to the fact that the maintenance fluid can be introduced into the closed breathing circuit of the closed-circuit breathing apparatus by means of the connection module, it can, furthermore, be achieved that the maintenance work will no longer come into contact with corrosive chemical media. This is only possible with the use of protective clothing for the maintenance worker in case of a conventional maintenance or treatment with disinfectants in case of an essentially fully disassembled closed-circuit breathing apparatus.

According to another aspect of the present invention, the connection module has an additional fluid inlet, through which a gas can be introduced into it for drying the closed breathing circuit. The gas for drying the closed breathing circuit may be compressed air from a line or from pressurized gas cylinders. The use of electric compressors for generating the gas for drying is also possible.

In another embodiment of the present invention, the connection module has a controller, valves that can be controlled and/or regulated by the controller, at least one fluid storage device filled with maintenance fluid, a fluid delivery device and a power supply unit, wherein the maintenance fluid can be delivered through the closed-circuit breathing apparatus by the controller by means of the fluid delivery device in a state in which the connection module is installed in the closed-circuit breathing apparatus. It is possible as a result to create a mobile maintenance module with a connection module operating independently from additional components. However, this solution is not limited to the mobile maintenance module, but may also be operated stationarily. The maintenance fluid in the at least one fluid storage device is preferably a disinfectant or water as a cleaning agent. For example, two fluid storage devices are provided in a preferred embodiment, one being filled with a disinfectant and the other with a rinsing and cleaning agent, for example, water or a fluid mixed with chemicals. The fluid storage devices may then be switched by means of valves such that first the cleaning agent and then the disinfectant can be discharged first into the closed breathing circuit of the closed-circuit breathing apparatus. The valves used for this are preferably shut-off valves, but they are not limited to these. For example, other stop valves, pressure valves, flow control valves or directional control valves may be used as well.

According to an advantageous variant, the connection module has, furthermore, at least one empty fluid storage device, and the maintenance fluid can be delivered into the empty fluid storage device by means of the fluid delivery device from the at least one filled fluid storage device through the fluid inlet, the closed-circuit breathing apparatus and the fluid outlet in that order. An especially mobile maintenance module, which does not rely on any external accessories, such as tanks or fluid sources, is created hereby. Due to the fact that the maintenance fluid, for example, disinfectant mixed with chemical substances, is not dispensed from the connection module, but is stored directly in same, the connection module may be used, in principle, at any point, without environmentally relevant precautionary measures having to be taken concerning correct discharge of the disinfectant.

The connection module according to the present invention may have a gas cylinder, from which gas can be discharged for drying the closed breathing circuit. It is possible as a result to create a mobile maintenance module not only for disinfecting and/or cleaning closed-circuit breathing apparatuses, but also for rapidly drying same. The gas can be delivered in this case by the controller through the closed-circuit breathing apparatus by means of a fluid delivery device in a state in which the connection module is installed in the closed-circuit breathing apparatus. However, the gas cylinder may also be designed as a pressurized gas cylinder, so that the gas can be introduced as compressed air into the closed breathing circuit without a fluid delivery device. It is also possible to use compressors to generate the gas for drying.

According to another aspect of the present invention, a maintenance device for closed-circuit breathing apparatuses with the above-described connection module is provided for accomplishing the object. The maintenance device contains a controller as well as valves that can be controlled and/or regulated by the controller, wherein the maintenance fluid and/or the gas can be circulated by the controller and the control and/or regulation of the valves through the closed breathing circuit in the state in which the connection module is installed in the closed-circuit breathing apparatus. It is possible by means of such a maintenance device to provide a maintenance device that can be transported relatively easily and can be connected to maintenance fluid sources, such as fluid tanks and/or fluid lines, and optionally to a power source only at the site of use, and it controls and/or regulates maintenance fluids through the closed breathing circuit of the closed-circuit breathing apparatus via the integrated controller and the corresponding valves.

The maintenance device may be preferably equipped for this with a temperature and/or humidity sensor in the area of the inlet port and in the area of the outlet port of the connection module. For example, the drying and the drying efficacy of the closed-circuit breathing apparatus can be monitored hereby. The inner surfaces of the closed breathing circuit can be recognized, for example, as dry when the measured temperatures and humidities are equal at the inlet and outlet of the connection module. The controller can then subject the sensor information detected to further processing and control and regulate the valves correspondingly.

The maintenance device according to the present invention may provide, furthermore, a filter module, the connection module being able to be mounted upstream at a regenerating cartridge of the closed-circuit breathing apparatus and the filter module downstream at the regenerating cartridge. The present invention is based in this connection on the discovery that breathing lime used in regenerating cartridges as an absorbent for chemically binding carbon dioxide contained in the exhaled air creates a highly alkaline medium after use. This means that the present invention utilizes according to this aspect the chemical, actually adverse properties of the breathing lime, as a result of which disinfection can be carried out. A highly alkaline medium, which develops due to the chemical absorption reaction of the breathing lime (pH value up to about 12), is present in the regenerating cartridge during and after the operation or use. Water, which flows through the regenerating cartridge, and is thus in contact with the breathing lime, immediately becomes highly alkaline. This highly alkaline liquid has a strongly inactivating effect reducing the count of bacteria, viruses and fungi. The geometric conditions prevailing in the regenerating cartridge (compacted breathing lime pills, screens and filters used) represent a mechanical trap for many of the bacteria and fungi that is hard to overcome. The disinfection process is supported by the trapping of the microorganisms. Sufficient disinfectant effect can be ensured for the closed-circuit breathing apparatus due to the superimposition of the mechanical and chemical properties of breathing lime with a thermal component. The thermal component comes into play when the water used, which flows through the regenerating cartridge, has a temperature above about 50° C. and preferably between 50° C. and 60° C. A temperature-regulating device may be provided for this in the maintenance device. The breathing lime used in regenerating cartridges has, moreover, neutral odor. The warm, highly alkaline liquid, which flows through the regenerating cartridge and disinfects the closed-circuit breathing apparatus, consequently also has neutral odor. Intensive rinsing after disinfection is consequently no longer necessary, as a result of which the water consumption can be reduced. The filter module, as well as the connection module do not have to be able to mounted directly on the regenerating cartridge, but they may also be connected to it via an intermediate element.

In a variant, the maintenance device may have a bypass line, which connects the connection module to the filter module. This means that the connection module is connected directly to the filter module such that a fluid flow can be routed around the regenerating cartridge. It is possible as a result to bypass the regenerating cartridge during a rinsing operation, for example, one carried out with water.

According to another aspect of the present invention, a closed-circuit breathing apparatus with the above-described connection module or with the above-described maintenance device is provided to accomplish the object. The same advantages that were already described in detail in connection with the connection module and the maintenance device apply in this case to the closed-circuit breathing apparatus.

According to yet another aspect of the present invention, a method is provided for maintaining a closed-circuit breathing apparatus, comprising the steps of opening the closed-circuit breathing apparatus at at least one point, installing the above connection module or the above maintenance device at the opened point, introduction of maintenance fluid into the closed breathing circuit of the closed-circuit breathing apparatus through the connection module or the maintenance device. The opening of the closed-circuit breathing apparatus represents in this case the opening of the closed breathing circuit, i.e., for example, a breathing tube is pulled off from a regenerating cartridge or a breathing tube is pulled off from a tube port of a breathing mask for opening the closed-circuit breathing apparatus.

The connection module is preferably mounted upstream at the regenerating cartridge of the closed-circuit breathing apparatus and the filter module is mounted downstream at the regenerating cartridge. For example, a disinfecting fluid and/or a cleaning fluid may be used as a maintenance fluid, first the cleaning fluid and then the disinfecting fluid being introduced for maintenance into the closed breathing circuit of the closed-circuit breathing apparatus. After introducing the disinfecting fluid, a gas may, furthermore, be introduced into the closed breathing circuit of the closed-circuit breathing apparatus for drying the closed breathing circuit. However, the maintenance operation is not limited to this. It is thus also conceivable that a rinsing operation, in which the closed breathing circuit is rinsed first with a rinsing fluid, for example, water, and is cleaned with the cleaning fluid, for example, cleaning fluid mixed with suitable chemicals, only thereafter. It is, furthermore, conceivable that an additional rinsing operation is carried out after the introduction of the disinfecting fluid before drying is started. The drying temperature and drying time must be adapted to the materials being used. A fluid circulation in a closed circuit is not necessary and is rather disadvantageous for drying the closed breathing circuit. The fluid outlet and/or the fluid inlet should therefore remain open during drying. To achieve gentle drying of the closed breathing circuit, it is recommended that a slow increase in the velocity of flow of the drying medium be set. The cyclic switching on and off of a drying blower or of a compressed air supply ensures a more efficient drying, because flexible components in the closed breathing circuit, such as breathing bag or directional control valves, will steadily remain in motion. To achieve an even better disinfecting effect, the maintenance fluid may, furthermore, be sent before entry into the inlet port through a UV generator to be provided preferably upstream of the connection module. The UV radiation is, for example, UV-C radiation in the wavelength range of 100 nm to 300 nm. In addition, it is conceivable for this that the maintenance fluid is additionally exposed to ultrasound vibrations by an ultrasound generator to be provided. The same advantageous effects that are obtained in case of the above connection module and/or the above maintenance device are obtained by the method according to the present invention for maintaining a closed-circuit breathing apparatus.

According to yet another aspect of the present invention, a maintenance system with a plurality of the above-mentioned connection modules or with a plurality of the above maintenance devices is provided for the automatic maintenance of closed-circuit breathing apparatuses according to the above method to accomplish the object. The maintenance system now comprises, for example, a control chamber and a cleaning chamber. The necessary lines, electrically and/or pneumatically controlled valves, water and air filters, dispensing units for liquid and/or powdered cleaning and/or disinfecting media, water and air heaters as well as the controller are present in the control chamber. The water needed for the cleaning and disinfection can then be taken either directly from a line or from fluid storage devices. It is preferable to decalcify the water in order to prevent lime residues from forming in the closed breathing circuit. As was already described above, the gas or drying medium may be compressed air from a line or from pressurized gas cylinders. The use of compressors to generate the drying medium is also possible. The drying temperature and drying time may be adapted to the materials used in the system. The controller coordinates the mode of operation of different actuators and valves in order to make it possible to clean, disinfect and dry one or more closed-circuit breathing apparatuses. The controller is also responsible for the automatic dispensing of the cleaning and/or disinfectant agents. The cleaning chamber may contain, for example, an additional nozzle system and a holding device. The nozzle system makes possible the cleaning, disinfection and drying of the outer surfaces of the closed-circuit breathing apparatuses. The holding device makes it possible to receive one or more closed-circuit breathing apparatuses as well as to treat the inner, breathing air-carrying surfaces in the system. It is preferred if the treating closed-circuit breathing apparatuses are in a horizontal position. This position is favorable for the fluid circulation in the closed circuit of the closed-circuit breathing apparatus. A fluid circulation in the closed breathing circuit makes a major contribution to the reduction of water consumption.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
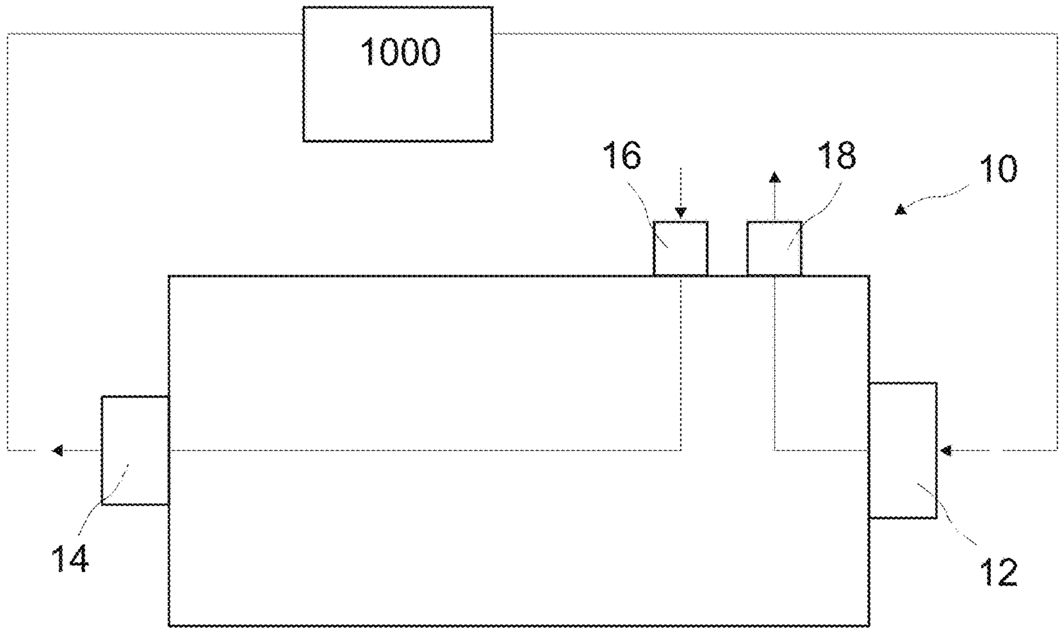
FIG. 1 is a schematic view of a connection module according to an embodiment of the present invention.

Referring to the drawings, elements having the same function and mode of action are always designated by the same reference numbers in FIGS. 1 through 8, and a redundant description of individual components is avoided.

FIG. 1 shows a schematic view of a connection module 10 according to an embodiment of the present invention. FIG. 1 shows especially a connection module 10 for installation in a closed breathing system of a closed-circuit breathing apparatus 1000 with an inlet port 12, at which a first closed circuit element of the closed-circuit breathing apparatus 1000 can be connected, with an outlet port 14, at which a second closed circuit element of the closed-circuit breathing apparatus 1000 can be connected, with at least one fluid inlet 16, through which maintenance fluid can be introduced into the closed breathing circuit of the closed-circuit breathing apparatus 1000, and with at least one fluid outlet 18, through which the maintenance fluid can be removed from the closed breathing circuit of the closed-circuit breathing apparatus 1000. The closed-circuit breathing apparatus 1000 is shown only schematically in FIG. 1. It is not shown in FIGS. 2 through 8 for a simplified representation. Valves, which may be located outside the connection module 10 or in it, may be provided for controlling and/or regulating the fluid flow in the connection module 10. The inlet port 12, the outlet port 14, the fluid inlet 16 and the fluid outlet 18 may project from a main surface of the connection module, but they may also be arranged such that they are placed into it. The positions of the inlets and outlets 12, 14, 16, 18 are not limited to those shown in FIG. 1.

Such a connection module 10 is especially significant for customers who have only a few closed-circuit breathing apparatuses 1000, or for those who rarely use such closed-circuit breathing apparatuses 1000. The acquisition of a large cleaning, disinfecting and drying device may not be economical for these customers. The connection module 10 may be used in this case from one respirator to the next and thus make possible a serial and cost-effective treatment.

Figure 2:
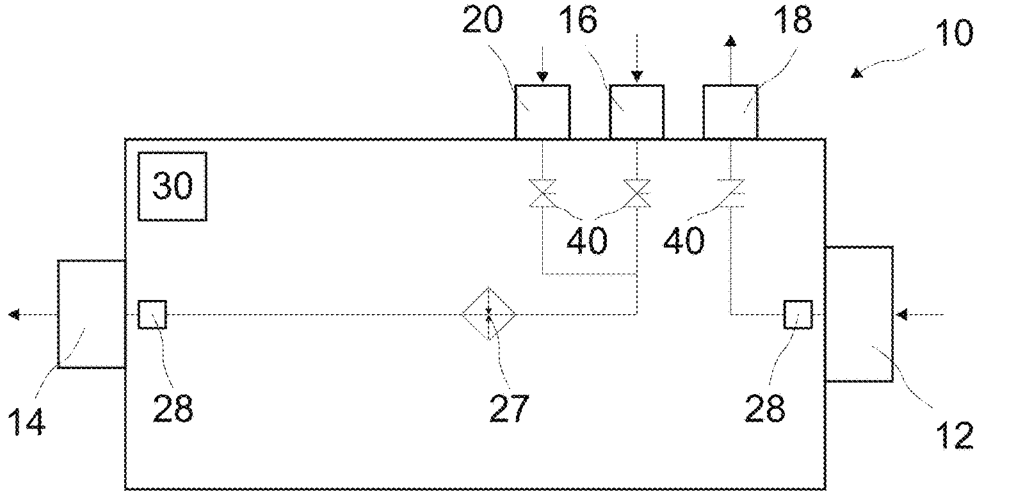
FIG. 2 is a schematic view of a connection module according to another embodiment of the present invention.

FIG. 2 shows a schematic view of a connection module 10 according to another embodiment of the present invention. The connection module 10 differs from the connection module 10 shown in FIG. 1 especially by an additional fluid inlet 20 for gas for drying the closed breathing circuit, as well as by the temperature and/or humidity sensors 28 and the valves 40. The drying and the drying efficacy of the closed-circuit breathing apparatus 1000 (FIG. 1) can be monitored by the temperature and/or humidity sensors 28. The inner surfaces of the closed breathing circuit can be recognized as being dry, for example, when the measured temperatures and humidities are equal at the inlet and outlet of the connection module 10. The controller 30 can then subject the detected sensor information to further processing and control or regulate the valves 40 correspondingly. A temperature control module 27, which controls the maintenance fluid to a desired temperature before it enters the closed breathing circuit of the closed-circuit breathing apparatus 1000 (FIG. 1), may be provided for heating the maintenance fluid.

Figure 3:
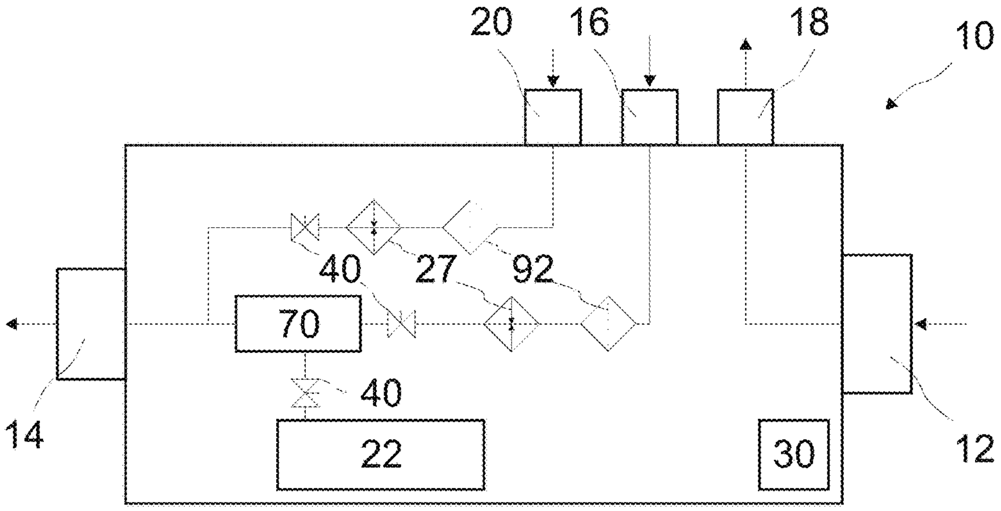
FIG. 3 is a schematic view of a connection module according to another embodiment of the present invention.

FIG. 3 shows a schematic view of a connection module 10 according to another embodiment of the present invention. The connection module 10 shown in FIG. 3 differs from the connection module 10 shown in FIG. 2 especially by the fluid storage device 22 as well as the dispensing unit 70. This embodiment is especially well suited for use in connection modules 10 that must treat only a single closed-circuit breathing apparatus 1000 (FIG. 1). The integrated dispensing unit 70 for liquid and/or powdered cleaning and/or disinfecting agents may be dimensioned as a much smaller unit than in case of stationary cleaning devices. As a result, the limited volume available for installation can be utilized optimally. The controller 30 coordinates in this case the mode of operation of the different valves 40 in order to make possible the cleaning, disinfection and drying of one or more closed-circuit breathing apparatuses 1000 (FIG. 1). The controller 30 is also responsible for the automatic dispensing of the cleaning and/or disinfecting agents. The controller 30 as well as the other electric components may be supplied with power either from a power grid or by means of integrated batteries. The particle filters 92 shown as an example in FIG. 3 are used to filter the maintenance fluid to be introduced into the closed breathing circuit and are optional components.

Figure 4:
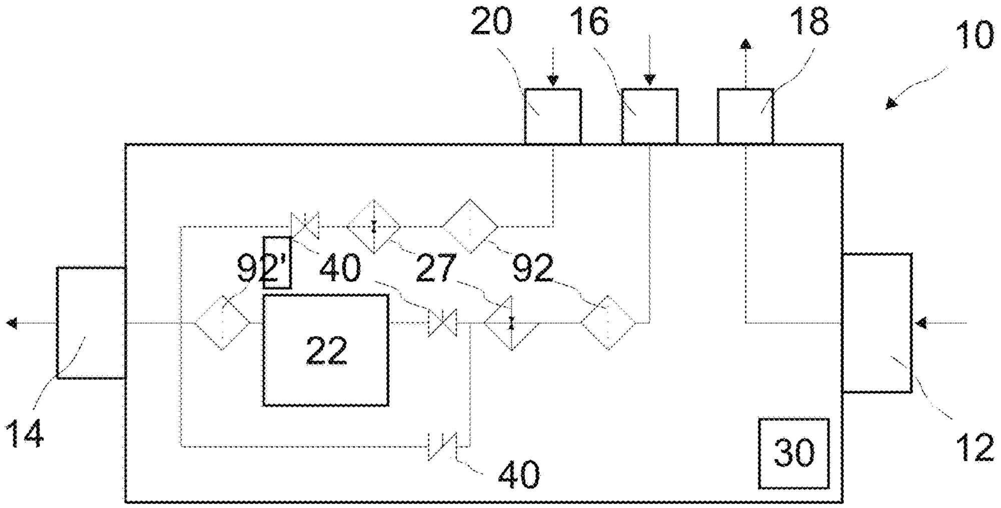
FIG. 4 is a schematic view of a connection module according to another embodiment of the present invention.

FIG. 4 shows a schematic view of a connection module 10 according to another embodiment of the present invention. The connection module 10 shown in FIG. 4 differs from the connection module 10 shown in FIG. 3 especially by the integrated fluid storage device 22 and the additional particle filter 92' arranged downstream of this. Especially the property of the so-called breathing lime is used in this case. The fluid storage device 22 may be filled with liquid and/or powdered cleaning and/or disinfecting agent, preferably breathing lime. For example, breathing lime may also be poured in this case into the fluid storage device 22 from a breathing lime cartridge. It is preferred to use a filter following the fluid storage device 22 in order to prevent the lime dust from being entrained into the other components of the closed breathing circuit.

Figure 5:
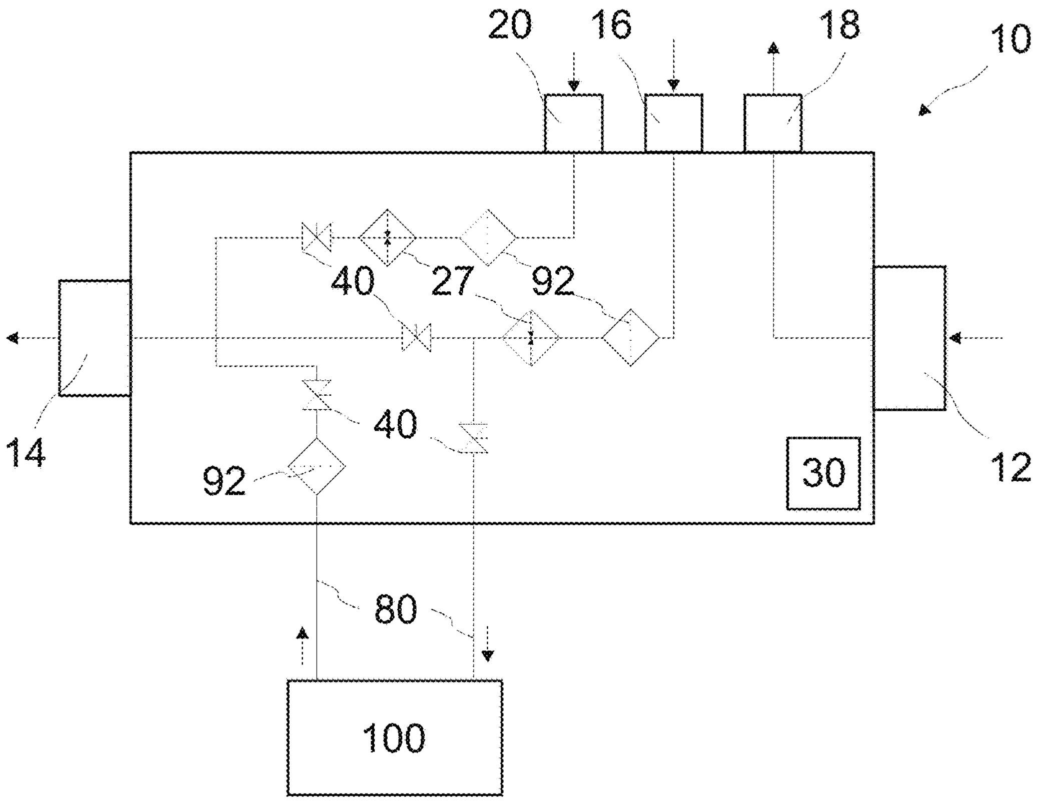
FIG. 5 is a schematic view of a connection module according to another embodiment of the present invention.

FIG. 5 shows a schematic view of a connection module according to another embodiment of the present invention. The connection module 10 shown in FIG. 5 differs from the connection module 10 shown in FIG. 5 especially by the regenerating cartridge 100 transferred to the outside. Unlike in the embodiment described in FIG. 4, the breathing lime does not have to be poured into a fluid storage device 22. The used regenerating cartridge 100 full of breathing lime is connected to external lines 80 of the connection module 10. The disinfecting effect of the lime present in the regenerating cartridge 100 is used due to the flow through the regenerating cartridge 100. If the regenerating cartridge 100 has more than two inlets and outlets, the additional outlets must be closed or sealed. It is avoided hereby that water will escape from the regenerating cartridge 100.

Figure 6:
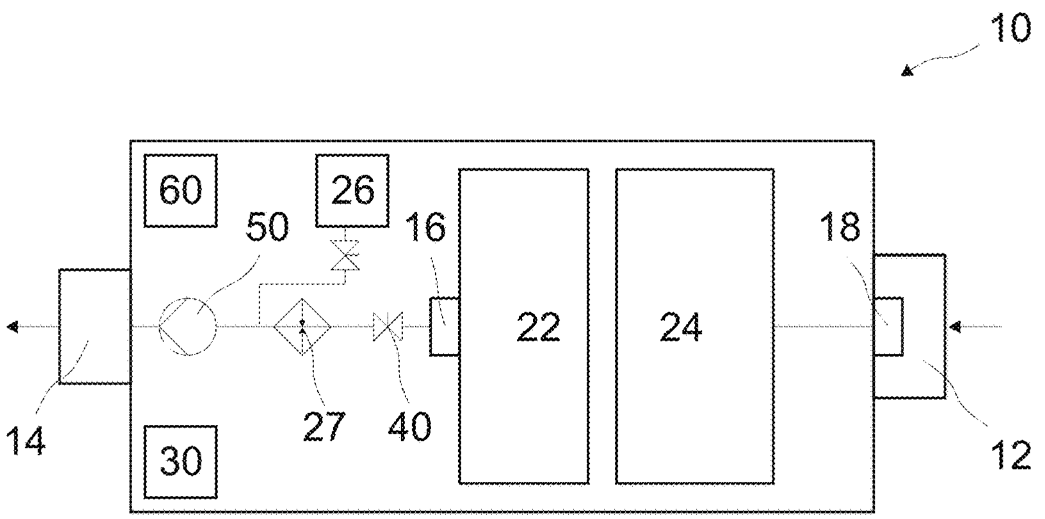
FIG. 6 is a schematic view of a connection module according to another embodiment of the present invention.

FIG. 6 shows a schematic view of a connection module 10 according to another embodiment of the present invention. In the embodiment shown in FIG. 6, the connection module 10 has the controller 30, valves that can be controlled and/or regulated by the controller 30, at least one fluid storage device 22 filled with maintenance fluid, a fluid delivery device 50 and a power supply unit 60. The maintenance fluid can be delivered through the closed-circuit breathing apparatus 1000 by means of the fluid delivery device 50 in a state in which the connection module 10 is installed into the closed-circuit breathing apparatus 1000. The maintenance fluid in at least one fluid storage device 22 is preferably a disinfectant or water as a cleaning agent. Two or more fluid storage devices 22 may also be provided in a preferred embodiment, one being filled with a disinfectant and other with a cleaning agent, for example, water. The fluid storage devices may then be connected via the valves 40 or the controller 30 such that first the disinfectant and then the cleaning agent can be discharged into the closed breathing circuit of the closed-circuit breathing apparatus 1000. The maintenance fluid removed from the fluid storage device 22 may subsequently be collected, for example, in an empty fluid storage device 24, which is likewise arranged in the connection module 10.

Furthermore, a gas cylinder, from which gas can be removed for drying the closed breathing circuit, is arranged in the embodiment shown in FIG. 6. Due to a connection module according to this embodiment, it is possible to create a mobile maintenance module not only for disinfecting and/or cleaning but also for rapidly drying closed-circuit breathing apparatuses 1000. The gas can be delivered in this case by the controller 30 through the closed-circuit breathing apparatus 1000 by means of the fluid delivery device 50 in a state in which the connection module 10 is installed in the closed-circuit breathing apparatus 1000. However, the gas cylinder 26 may also be designed, for example, as a pressurized gas cylinder, so that the gas can be introduced as compressed air into the closed breathing circuit without a fluid delivery device 50. The use of electric compressors is also possible. The fluid outlet 18 is a fluid outlet with respect to the closed breathing circuit of the closed-circuit breathing apparatus 1000 in this case, i.e., the maintenance fluid can be discharged from the closed breathing circuit of the closed-circuit breathing apparatus 1000 through the fluid outlet 18 and it can enter the connection module or the empty fluid storage device 24.

Figure 7:
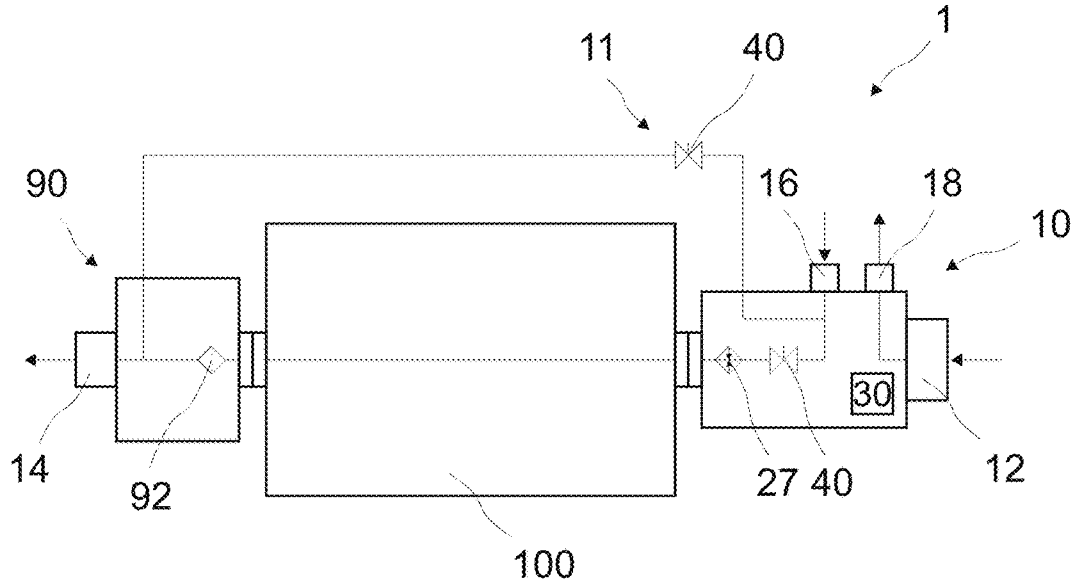
FIG. 7 is a schematic view of a maintenance device according to an embodiment of the present invention.

FIG. 7 shows a schematic view of a maintenance device 1 according to an embodiment of the present invention. In particular, FIG. 7 shows a device for the thermochemical disinfection of closed-circuit breathing apparatuses 1000, which use breathing lime as an absorbent for chemically binding carbon dioxide contained in the exhaled air. The maintenance device 1 according to the present invention utilizes in this case the chemical, actually adverse properties of the breathing lime to carry out the disinfection. A highly alkaline medium, which develops due to the chemical absorption reaction of the breathing lime, develops in the regenerating cartridge 100 during and after use. It was possible to experimentally demonstrate during the development of the present invention that water, which flows through the regenerating cartridge 100 and has thus contact with the breathing lime, becomes immediately highly alkaline. This highly alkaline liquid has a strongly inactivated effect and reduces the count of bacteria, viruses and fungi.

The maintenance device 1 according to the present invention according to this embodiment is provided with the above-described connection module 10. The maintenance device 1 contains, furthermore, a controller 30 as well as valves 40 that can be controlled and/or regulated by the controller, wherein the maintenance fluid and/or the gas can be circulated through the closed breathing circuit by the controller 30 and the control and/or regulation of the valves 40 in a state in which the connection module 10 is installed in the closed-circuit breathing apparatus 1000. The connection module 10 is mounted in the maintenance device 1 upstream at the regenerating cartridge 100. A filter module 90 is mounted downstream at the regenerating cartridge 100. The connection module 10 is preferably plugged in there between an exhalation tube (not shown) and the regenerating cartridge 100 filled at least partially with breathing lime. The connection module 10 will then connect the closed-circuit breathing apparatus 1000 to a water supply via the fluid inlet 16 and, for example, to the sewer system or a wastewater site via the fluid outlet 18.

The water needed for the disinfection may be taken in this case again either directly from a line or from fluid containers or tanks. The water used for the disinfection may then be heated continuously to a certain temperature, for example, above 50° C., preferably between 50° C. and 60° C., by means of an electric heating module 27. The filter module 90 is then mounted between the regenerating cartridge 100 and a breathing bag (not shown). The filter module 90 contains suitable particle filters 92 in order to prevent the entrainment of the lime dust from the regenerating cartridge 100 into the other components of the closed breathing circuit.

Only the valve 40 in the connection module 10 must be opened to disinfect the closed breathing circuit. Water, which flows through the regenerating cartridge 100, immediately becomes highly alkaline and ensures the disinfection of the remaining components of the closed breathing circuit. The highly alkaline liquid then flows back via the exhalation tube, for example, into the sewer system. It is also possible to reuse this liquid to lower water consumption.

To rinse the closed breathing circuit with fresh water, the valve 40 in the connection module 10 is closed and the valve 40 in the bypass line 11 is opened. This makes it possible to bypass the regenerating cartridge 100. The control of the different valves takes place fully automatically in this case.

The above-described devices for thermochemical disinfection may be designed both as stationary and portable variants. Tanks for maintenance fluid as well as a built-in power supply unit must be present in the portable variant.

Figure 8:
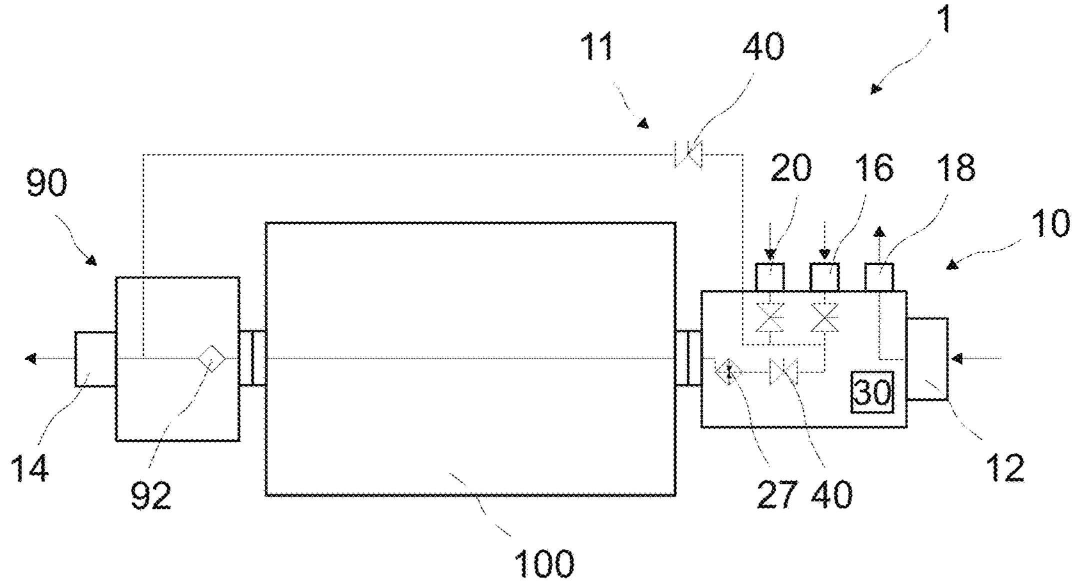
FIG. 8 is a schematic view of a maintenance device according to another embodiment of the present invention.

FIG. 8 shows a schematic view of a maintenance device according to another embodiment of the present invention. The maintenance device shown in FIG. 8 differs from the maintenance device shown in FIG. 7 especially by the additional fluid inlet for gas for drying the closed breathing circuit and a correspondingly necessary circuit along with additional valves 40.

It is advantageous for optimal maintenance if the cleaning and disinfection are repeated several times. It is ensured hereby that even small components will be treated sufficiently. The cyclic filling and emptying of the closed breathing circuit is used, furthermore, to better reach poorly accessible surfaces carrying breathing air in order to achieve better wetting with the maintenance fluid, i.e., the cleaning and/or disinfecting agent.

Additional components, which make a pressure exchange with the surrounding area possible, for example, a water drain valve or a pressure relief valve, may be provided at the connection module 10 or at the maintenance device 1 in all the above-described embodiments. These are known in detail in the state of the art and they are not therefore described here in detail. These valves must, in principle, be closed during the circulation of a maintenance fluid. Fluid circulation in closed circuit is not necessary and is rather disadvantageous for drying the closed breathing circuit. Valves, such as a pressure relief valve or a water drain valve, but also valves arranged upstream of the fluid outlet 18, may therefore remain open during drying. A slow increase in the velocity of flow of the drying medium is advantageous for gentle drying of the closed breathing circuit. A cyclic switching on and off of the drying blower or of the compressed air supply ensures efficient during, because flexible components in the closed breathing circuit, for example, the breathing bag or directional control valves, remain steadily in motion.

The valves 40 described are coordinated by the controller 30 fully automatically in the known manner. Reproducible quality of cleaning, disinfection and drying is thus guaranteed.

While specific embodiments of the invention have been shown and described in detail to illustrate the application of the principles of the invention, it will be understood that the invention may be embodied otherwise without departing from such principles.

APPENDIX

List of Reference Numbers

| | |
|---|---|
| 1 | Maintenance device |
| 10 | Connection module |
| 11 | Bypass line |
| 12 | Inlet port |
| 14 | Outlet port |
| 16 | Fluid inlet for maintenance fluid |
| 18 | Fluid outlet for gas/maintenance fluid |
| 20 | Fluid inlet for gas |
| 22 | Filled fluid storage device |
| 24 | Empty fluid storage device |
| 26 | Gas cylinder |
| 27 | Temperature control module |
| 28 | Temperature and/or humidity sensor |
| 30 | Controller |
| 40 | Valves |
| 50 | Fluid delivery device |
| 60 | Power supply unit |
| 70 | Dispensing unit |
| 80 | External lines |
| 90 | Filter module |
| 92, 92' | Particle filter |
| 100 | Regenerating cartridge |
| 1000 | Closed-circuit breathing apparatus |

What is claimed is:

1. A connection module for installation in a closed breathing circuit of a closed-circuit breathing apparatus, the connection module comprising:
- an inlet port, at which a first closed circuit element of the closed-circuit breathing apparatus is to be connected;
- an outlet port, at which a second closed circuit element of the closed-circuit breathing apparatus is to be connected;
- at least one fluid inlet through which maintenance fluid is introduced into the closed breathing circuit of the closed-circuit breathing apparatus; and
- at least one fluid outlet through which the maintenance fluid is removed from the closed breathing circuit of the closed-circuit breathing apparatus.

2. A connection module in accordance with claim 1, further comprising an additional fluid inlet through which a gas is introduced into the closed breathing circuit of the closed-circuit breathing apparatus for drying the closed breathing circuit.

3. A connection module in accordance with claim 1, further comprising:
- a controller;
- valves at least one of controlled and regulated by the controller;

at least one fluid storage device with the maintenance fluid;

a fluid delivery device; and a power supply unit, wherein the maintenance fluid is delivered through the closed-circuit breathing apparatus by the controller by means of the fluid delivery device in a state in which the connection module is installed in the closed-circuit breathing apparatus.

4. A connection module in accordance with claim 3, further comprising at least one empty fluid storage device, wherein the maintenance fluid is delivered into the empty fluid storage device by means of the fluid delivery device in an order comprising from the at least one filled fluid storage device, through the fluid inlet, through the closed-circuit breathing apparatus and through the fluid outlet.

5. A connection module in accordance with claim 3, further comprising a gas cylinder, from which gas can be removed for drying the closed breathing circuit.

6. A connection module in accordance with claim 1, in combination with at least another connection module to provide a plurality of connection modules forming a maintenance system with the plurality of connection modules providing automatic maintenance of closed-circuit breathing apparatuses comprising closed-circuit elements, wherein the maintenance system further comprises a plurality of fastening devices wherein each connection module is plugged, screwed, brought into contact and/or mounted in a positive-locking manner by the fastening means, between two of the closed-circuit elements.

7. A maintenance device for closed-circuit breathing apparatuses, the maintenance device comprising:

a connection module comprising an inlet port, at which a first closed circuit element of the closed-circuit breathing apparatus is to be connected, an outlet port, at which a second closed circuit element of the closed-circuit breathing apparatus is to be connected, at least one fluid inlet through which maintenance fluid is introduced into the closed breathing circuit of the closed-circuit breathing apparatus, and at least one fluid outlet through which the maintenance fluid is removed from the closed breathing circuit of the closed-circuit breathing apparatus;

a controller; and valves at least one of controlled and regulated by the controller, wherein the maintenance fluid can be circulated by the controller with one of the control and regulation of the valves through the closed breathing circuit in a state in which the connection module is installed in the closed-circuit breathing apparatus.

8. A maintenance device for closed-circuit breathing apparatuses in accordance with claim 7, further comprising at least one of a temperature and a humidity sensor provided in an area of the inlet port and in an area of the outlet port of the connection module.

9. A maintenance device for a closed-circuit breathing apparatus in accordance with claim 7, further comprising a filter module, wherein the connection module is mountable upstream at a regenerating cartridge of the closed-circuit breathing apparatus and the filter module is mountable downstream at the regenerating cartridge.

10. A maintenance device for a closed-circuit breathing apparatus in accordance with claim 9, further comprising a bypass line connecting the connection module to the filter module.

11. A maintenance device for a closed-circuit breathing apparatus in accordance with claim 7, further comprising an additional fluid inlet through which a gas is introduced into the closed breathing circuit of the closed-circuit breathing apparatus for drying the closed breathing circuit.

12. A maintenance device for a closed-circuit breathing apparatus in accordance with claim 7, further comprising:

at least one fluid storage device with the maintenance fluid;

a fluid delivery device; and a power supply unit, wherein the maintenance fluid is delivered through the closed-circuit breathing apparatus by the controller acting on the fluid delivery device in a state in which the connection module is installed in the closed-circuit breathing apparatus.

13. A maintenance device for a closed-circuit breathing apparatus in accordance with claim 12, further comprising at least one empty fluid storage device, wherein the maintenance fluid is delivered into the empty fluid storage device by means of the fluid delivery device in an order comprising from the at least one filled fluid storage device, through the fluid inlet, through the closed-circuit breathing apparatus and through the fluid outlet.

14. A maintenance device for a closed-circuit breathing apparatus in accordance with claim 12, further comprising a gas cylinder, from which gas can be removed for drying the closed breathing circuit.

15. A closed-circuit breathing apparatus comprising:

closed-circuit elements; and a connection module comprising:

an inlet port, at which a first closed circuit element of the closed-circuit breathing apparatus is to be connected;

an outlet port, at which a second closed circuit element of the closed-circuit breathing apparatus is to be connected;

at least one fluid inlet through which maintenance fluid is introduced into the closed breathing circuit of the closed-circuit breathing apparatus;

at least one fluid outlet through which the maintenance fluid is removed from the closed breathing circuit of the closed-circuit breathing apparatus; and a fastening device wherein the connection module is plugged, screwed, brought into contact and/or mounted in a positive-locking manner by the fastening means, between two of the closed-circuit elements.

16. A closed-circuit breathing apparatus in accordance with claim 15, wherein the connection module is part of a maintenance device that further comprises:

a controller;

valves at least one of controlled and regulated by the controller;

at least one fluid storage device with the maintenance fluid;

a fluid delivery device; and a power supply unit, wherein the maintenance fluid is delivered through the closed-circuit breathing apparatus by the controller by means of the fluid delivery device in a state in which the connection module is installed in the closed-circuit breathing apparatus.

* * * * *